United States Patent [19]

Fike et al.

[11] Patent Number: 5,364,784
[45] Date of Patent: Nov. 15, 1994

[54] METHOD FOR DELIVERING OXYGEN TO A CELL CULTURE MEDIUM

[75] Inventors: Richard Fike, Clarence; James M. Kubiak, Lancaster, both of N.Y.

[73] Assignee: Life Technologies, Inc., Gaithersburg, Md.

[21] Appl. No.: 972,366

[22] Filed: Nov. 5, 1992

Related U.S. Application Data

[62] Division of Ser. No. 691,801, Apr. 26, 1991, Pat. No. 5,268,298.

[51] Int. Cl.$^5$ ............................................. C12N 5/00
[52] U.S. Cl. .......................... 435/240.1; 435/240.25; 435/818
[58] Field of Search ............ 435/240.1, 240.2, 240.22, 435/240.241, 240.242, 240.25, 243, 240.3, 240.31, 284–286, 311, 313, 314, 315, 813, 818, 819; 261/122; 55/37, 84, 89, 90, 220, 227, 228, 229, 233, 240

[56] References Cited

U.S. PATENT DOCUMENTS

| | | | |
|---|---|---|---|
| 3,821,087 | 6/1974 | Knazek et al. | 435/313 |
| 4,220,725 | 7/1980 | Knazek et al. | 435/285 |
| 4,720,462 | 1/1988 | Rosenson | 435/285 |
| 4,749,654 | 6/1988 | Karrer et al. | 435/286 |

FOREIGN PATENT DOCUMENTS 0164813  12/1986  European Pat. Off. .

*Primary Examiner*—Michael G. Wityshyn
*Assistant Examiner*—William H. Beisner
*Attorney, Agent, or Firm*—Sterne, Kessler, Goldstein & Fox

[57] ABSTRACT

An apparatus and method for delivering oxygen to a cell culture medium is disclosed. In one embodiment, the apparatus includes a transfer chamber placed within the cell culture medium. The transfer chamber is adapted to allow the cell culture medium to come in substantial contact with a liquid chemical that is passing through transfer chamber. The apparatus further includes a vessel placed outside the cell culture medium that serves to contain and continually recharge the liquid chemical. The apparatus further includes a plurality of pumps and tubes for circulating the liquid chemical through the transfer chamber and back to the vessel. When the liquid chemical comes into contact with the cell culture medium, oxygen is transferred from the liquid chemical to the cell culture medium.

7 Claims, 2 Drawing Sheets

METHOD FOR DELIVERING OXYGEN TO A CELL CULTURE MEDIUM

This application is a divisional of application Ser. No. 07/691,801, filed Apr. 26, 1991, now U.S. Pat. No. 5,268,298.

FIELD OF THE INVENTION

The present invention relates generally to oxygen delivery systems. More particularly, the present invention relates to oxygen delivery systems that utilize liquid chemicals such as perfluorocarbons.

BACKGROUND OF THE INVENTION

Cell cultures need oxygen to grow. In low density cultures, such as cell culture growth in a flask, oxygen is delivered from the head space alone. The head space is defined as the area between the top of the container and the surface of the culture medium. However, where cultures are supplemented or are grown in a large volume, it is difficult for oxygen to be delivered throughout the culture medium by headspace alone.

Several systems have been developed for improving oxygen delivery to the cell cultures. One such system principally employs a "sparging ring." A sparging ring is a tube formed in a circle. The tube has many tiny holes. The tube is placed at the bottom of the culture vessel and extends outside to an oxygen supply. As oxygen is pumped into the sparging ring, air bubbles are introduced to the cell cultures at the bottom of the culture vessel. As the air bubbles rise, oxygen is delivered to the cell cultures throughout the culture vessel.

Oxygen delivery systems of this type, however, have several disadvantages. First, oxygen delivery via air bubbles may cause physical disruption of the cell membranes especially at higher impeller speeds. Additionally, air bubbles cause the formation of foam which may trap cells, degrade product and plug exit filters.

Another type of oxygen delivery system uses gas permeable tubing. In this system, pliable silicon tubing is wrapped around the inside of the culture vessel. The silicon tubing, unlike the sparging ring, has no holes. The gas permeable nature of the silicon allows oxygen to diffuse through the tubing and into the cell culture medium without the introduction of air bubbles.

Oxygen delivery systems of this type, however, also have several disadvantages. First, because of the quantity of tubing necessary to maintain satisfactory oxygen delivery, it is not practical to use gas permeable tubing for industry use. Second, to insure the absence of pin holes, the silicon tubing needs to be replaced routinely, a chore in itself.

Another type of oxygen delivery system involves emulsifying a liquid chemical and suspending it in the cell culture medium. The liquid chemical has the capacity of binding or collecting oxygen in an oxygen rich environment and liberating oxygen in an oxygen deficient environment. Some liquid chemicals also have a reciprocal relationship to $CO_2$. In other words, the liquid chemicals will absorb $CO_2$ in a $CO_2$ rich environment and liberate $CO_2$ in a $CO_2$ deficient environment. One common chemical used in such a system is perfluorocarbon (PFC) of which a number of varieties exist. The exact chemical is not essential as long as the chosen liquid chemical absorbs oxygen in an oxygen rich environment and gives it up in a deficient environment.

Oxygen delivery systems of this type, however, also have disadvantages. First, emulsion systems require high concentrations of emulsion in order to provide the necessary oxygen transfer. High concentrations of emulsion increases the risk of chemical contamination to the cell culture due to the various detergents, etc. required. Second, the oxygen delivery process is limited to internal re-oxygenation; the emulsion receives the oxygen from the sparging ring and the head space only, and thereafter delivers it to the cell cultures. This process is not as practical as external oxygenation where the regeneration process can be manipulated as need be. Third, emulsified PFC cannot be readily recycled or retained as in perfusion experiments. As such, the PFC must be continuously replaced at a very high cost.

Another type of oxygen delivery system involves the introduction of a non-emulsified PFC. In systems of this type, oxygenated PFC is introduced to the inside of the cell culture where it liberates oxygen and collects $CO_2$. Thereafter, the de-oxygenated PFC is transported to the outside where it is "recharged" with oxygen. In essence, the PFC is recycled. In this system, the PFC is sprayed by a nozzle into the head space. Because the PFC is a hydrophobic substance with densities higher than water, it does not mix with water. As such, the PFC falls to the bottom of the culture vessel. A tube at the bottom of the culture vessel is provided to remove the PFC for recycling.

Oxygen delivery systems of this type, however, also have disadvantages. First, the PFC is sprayed throughout the culture medium, and as such, collects at various points on the bottom of the culture vessel. Collection of the PFC with a tube thus becomes difficult, requiring a different configuration for each different bioreactor. Second, spraying of the PFC may cause damage to the cell membranes or generate foam. Third, of necessity, cells must directly contact the PFC which may not always be desirable.

SUMMARY OF THE INVENTION

The present invention is an apparatus/system and method for delivering oxygen to a cell culture medium. The oxygen delivery system and method of the present invention provides advantages heretofore unavailable in conventional oxygen delivery systems. As will become apparent to one skilled in the art, the oxygen delivery system and method to be described can be easily configured in alternative embodiments or carried out in other ways without departing from the spirit or scope of the invention.

In one embodiment, the oxygen delivery system of the present invention comprises a transfer chamber that is submerged in the cell culture medium. The transfer chamber is provided so that a liquid chemical can enter and leave the cell culture medium without the introduction of air bubbles. The oxygen delivery system further comprises a vessel placed outside the cell culture. The vessel provides a reservoir for the liquid chemical. The oxygen delivery system further comprises means for circulating the liquid chemical through the transfer chamber and back to the second vessel. The oxygen delivery system further comprises means for "recharging" the liquid chemical contained in the vessel.

The liquid chemical has the characteristic of collecting or binding oxygen in an oxygen rich environment, and giving up oxygen in an oxygen deficient environment. In this embodiment, the liquid chemical is perfluorocarbon. However, many other chemicals having similar, better or worse properties could be used. One such alternative liquid chemical is silicone oils.

The transfer chamber comprises an inlet portion and an outlet portion. The transfer chamber further comprises a culture permeable portion that allows cell culture medium to come in substantial contact with the liquid chemical to thereby cause oxygen delivery from the liquid chemical to the cell culture medium. The inlet portion, the outlet portion, and the culture permeable portion are formed from one piece. The culture permeable portion is a mesh screen. The mesh screen may be of a wide range of meshes, and at the lower end of the range, will prevent cells from entering the transfer chamber.

The circulating means comprises a first and second pump each having a suction side and a discharge side. The circulating means further comprises a first tube, a second tube, a third tube, and a fourth tube. The first and second tubes are connected with the first pump to thereby supply the liquid chemical from the vessel to the transfer chamber. The third and fourth tubes are connected with the second pump to thereby return the liquid chemical from the transfer chamber back to the vessel where recharging occurs.

BRIEF DESCRIPTION OF THE DRAWINGS

The following detailed description will be more fully understood with reference to the accompanying drawings in which.

DETAILED DESCRIPTION OF THE PREFERRED EMBODIMENT

Figure 1:
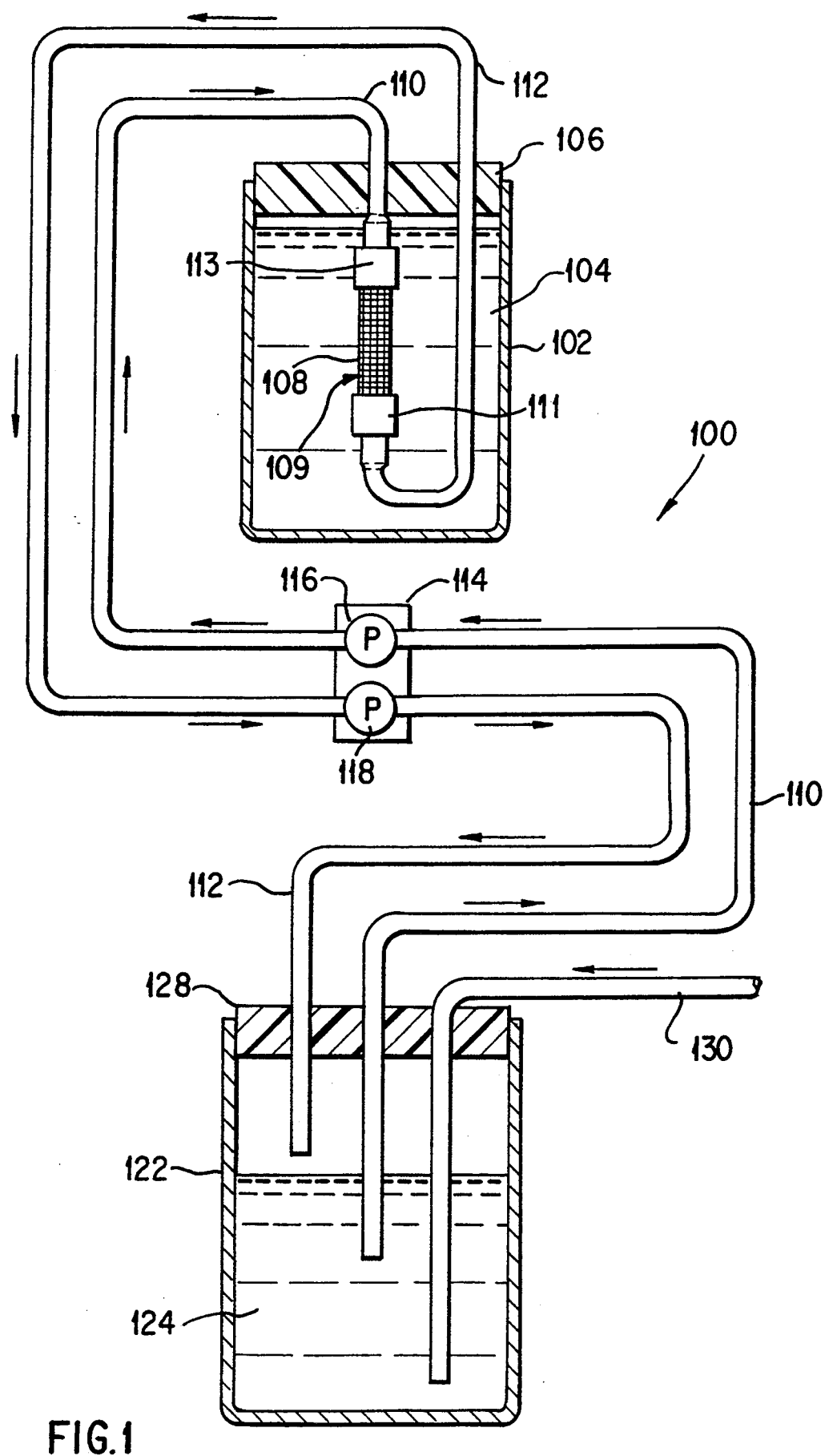
FIG. 1 is a schematic of a first embodiment of the present invention.

Referring first to FIG. 1 wherein a first embodiment of the oxygen delivery system 100 is shown. Oxygen delivery system 100 first comprises a first vessel 102 capable of holding a culture medium 104. First vessel 102 may take the form of what is commonly referred to as a bioreactor. A cover 106 is provided to enclose first vessel 102.

Oxygen delivery system 100 further comprises a second vessel 122 capable of holding a liquid chemical 124. In the preferred embodiment, the liquid chemical 124 is perfluorocarbon. It is contemplated that any of a number of liquid chemicals could be employed in the present invention. The only requirement is that the liquid chemical 124 exhibit the characteristic of giving up oxygen in an oxygen deficient environment and collecting (or binding) oxygen in an oxygen rich environment. Such other liquid chemicals include, but are not limited to, perfluorocarbons. A cover 128 is provided to enclose the second vessel 122. Although not shown, cover 128 may be formed with a filtered vent hole so as to allow the second vessel 122 to vent.

Oxygen delivery system 100 further comprises a transfer chamber 108 submerged in the culture medium 104. Transfer chamber 108 is generally provided to bring the liquid chemical 124 in substantial contact with the culture medium 104. In the preferred embodiment, transfer chamber 108 is formed with an inlet portion 113, an outlet portion 111, and a culture permeable portion 109. The culture permeable portion 109 allows the culture medium 104 to pass therethrough and thereby come in contact with the liquid chemical 124 passing through the transfer chamber 108.

In the preferred embodiment, the culture permeable portion 109 is a mesh screen having a porosity of approximately 400μ. However, smaller meshes that would keep biological cells from entering the transfer chamber 108 may be used. By way of example only, such alternative mesh porosities may be about 5μ. It is contemplated that culture permeable portion 109 could take a variety of forms. The only important design factor is that the culture permeable portion 109 allow the liquid chemical 124 to come in substantial contact with the culture medium 104 so as to transfer oxygen from the liquid chemical 124 to the culture medium 104.

The liquid chemical 124 enters the transfer chamber 108 at the inlet portion 113. The liquid chemical 124 exits the transfer chamber 108 at the outlet portion 111. In the preferred embodiment, the liquid chemical 124 is continually passed through the transfer chamber 108.

The oxygen delivery system 100 further comprises a multi-pump member 114. Multi-pump member 114 of the preferred embodiment is a peristaltic pump. Peristaltic pumps are well known in the art and provide a closed system for pumping fluids. Multi-pump member 114 comprises a first pump 116 and a second pump 118.

First pump 116 is provided to pump the liquid chemical 124 from the second vessel 122 to the transfer chamber 108. This is accomplished with a tube 110 working in concert with first pump 116. Tube 110 is connected at one end to the inlet portion 113 of transfer chamber 108. The other end of tube 110 is located within the liquid chemical 124 contained in second vessel 122.

Second pump 118 is provided to return the liquid chemical 124 from the transfer chamber 108 to the second vessel 122. This is accomplished by a tube 112 working in concert with second pump 118. Tube 112 is connected at one end to the outlet portion 111 of transfer chamber 108. The other end of tube 112 is placed within the second vessel 122.

The oxygen delivery system 100 of the present invention further comprises an oxygen supply tube 130. Oxygen supply tube 130 is provided to supply oxygen to the liquid chemical 124 contained in second vessel 122. The liquid chemical 124 that is returned from the transfer chamber 108 is depleted of oxygen. The introduction of oxygen via oxygen supply tube 130 "recharges" the liquid chemical 124. One end of oxygen supply tube 130 is connected to an oxygen supply source (not shown). The other end of the oxygen supply tube 130 is placed within the liquid chemical 124 of the second vessel 122.

The operation of the oxygen delivery system 100 of the present invention will now be described.

Initially a predetermined quantity of liquid chemical 124 is introduced into the second vessel 122. The quantity of liquid chemical 124 is based on the size of the second vessel 124, tube lengths, flow rates, and other similar design criteria.

Thereafter, the first and second pumps 116, 118, respectively, are turned on. Pumps 116 and 118 are set to the same operating characteristics. This is necessary to ensure a constant flow of liquid chemical 124 throughout the oxygen delivery system 100. Peristaltic pumps are ideal for this requirement.

Upon activation of first pump 116 and second pump 118, liquid chemical 124 contained in the second vessel 122 is drawn through tube 110 and into the transfer chamber 108. The liquid chemical 124 then passes under the force of gravity through the transfer chamber 108. While falling through the transfer chamber 108, the liquid chemical 124 (which is significantly denser than water) comes in contact with the cell culture medium 104 via permeable portion 109.

Thereafter, the liquid chemical 124, which is now oxygen deficient, is withdrawn from the transfer chamber 108 and dumped back into second vessel 122 via tube 112. The oxygen deficient liquid chemical 124 is then "recharged" by the oxygen introduced to second vessel by oxygen supply tube 130. Thereafter, the oxygen rich liquid chemical 124 is then recirculated back to the transfer chamber 108 as described previously.

Figure 2:
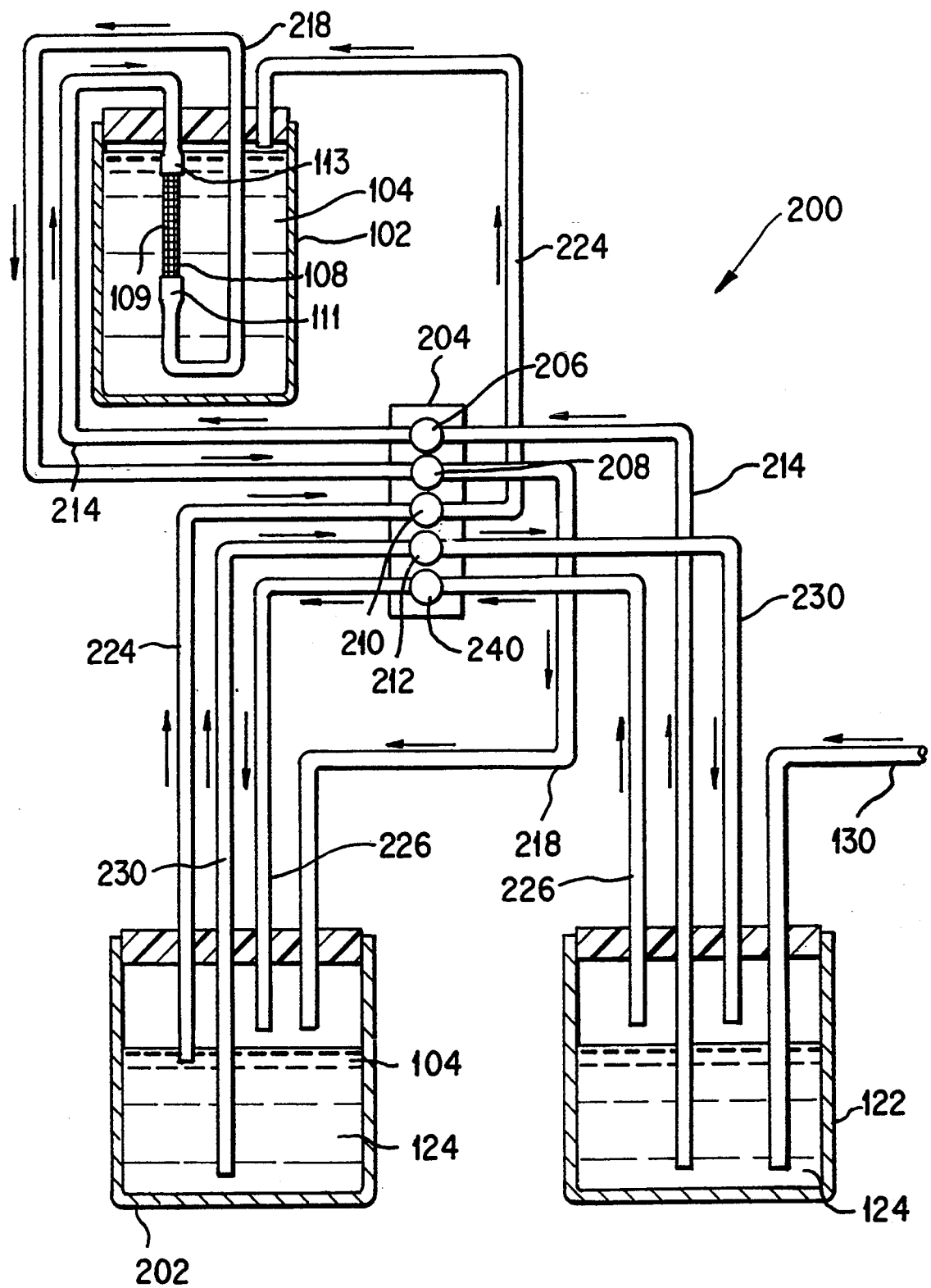
FIG. 2 is a schematic of a second embodiment of the present invention.

Referring next to FIG. 2, wherein a second embodiment of the present invention is shown. The second embodiment is denoted as oxygen delivery system 200. Oxygen delivery system 200 comprises a first vessel 102, a second vessel 122, and a transfer chamber 108. First vessel 102, second vessel 122, and transfer chamber 108 are of the same design and function as that shown and described with reference to FIG. 1.

Oxygen delivery system 200 further comprises a third vessel 202. Third vessel 202 is generally provided to separate culture medium that may have mixed with the liquid chemical during contact in the transfer chamber 108. As stated earlier, in the preferred embodiment, the liquid chemical 124 is PFC. PFC is a hydrophobic substance denser than water and, as such, falls to the bottom of the third vessel 202. Any cell culture medium 104 stays at the upper region of the third vessel 202.

Oxygen delivery system 200 further comprises a multi-pump member 204. Multi-pump member 204 like multi-pump member 114, is also a peristaltic pump. Multi-pump member 204 comprises a first pump 206, a second pump 208, a third pump 210, a fourth pump 212, and a fifth pump 240.

First pump 206 is provided to pump the liquid chemical 124 from the second vessel 122 to the transfer chamber 108. This is accomplished by a tube 214 acting in concert with first pump 206. One end of tube 214 is connected to the inlet portion 113 of transfer chamber 108. The other end of the tube 214 is placed within the liquid chemical 124 contained in second vessel 122.

Second pump 208 is provided to pump the liquid chemical 124, now oxygen deficient, from the transfer chamber 108 to the third vessel 202. This is accomplished by a tube 218. Tube 218 is connected at one end to the outlet portion 111 of transfer chamber 108. The other end of tube 218 is placed within the third vessel 202.

Third pump 210 is provided to return the culture medium present in the third vessel 202 back to the first vessel 102. This is accomplished by a tube 224. One end of tube 224 is paced at the upper region of the first vessel 102. The other end of tube 224 is placed within the third vessel 202.

Fourth pump 212 is provided to return the liquid chemical 124 from the third vessel 202 to the second vessel 122. This is accomplished by a tube 230. One end of tube 230 is placed at the lower portion of the third vessel 202. The other end of tube 230 is placed within the second vessel 122.

Fifth pump 240 is provided to maintain a predetermined level of liquid chemical 124 in the third vessel 202. This is necessary to prevent PFC from becoming depleted in vessel 202 and thus cell culture medium 104 from being pumped from vessel 202 to vessel 122. This is accomplished by a tube 226. One end of tube 226 is placed within the second vessel 122. The other end of tube 226 is placed within the third vessel 202.

The operation of oxygen delivery system 200 will now be described.

Initially a predetermined quantity of liquid chemical 124 is introduced into the second vessel 122 and third vessel 202. The quantity of liquid chemical 124 is based on the size of the second vessel 124 and third vessel 202, tube lengths, flow rates, and other similar design criteria obvious to one of ordinary skill in the art.

Thereafter, the first pump 206, second pump 208, third pump 210, fourth pump 212, and fifth pump 240 are turned on. First pump 206, second pump 208, third pump 210, fourth pump 212, and fifth pump 240 are set to the same operating characteristics. This is necessary to ensure a constant flow of liquid chemical 124 throughout the oxygen delivery system 200.

Activation of the pumps causes the liquid chemical 124 contained in the second vessel 122 to be drawn through tube 214 and into the transfer chamber 108. The liquid chemical 124 then passes under the force of gravity through the transfer chamber 108. While falling through the transfer chamber 108, the liquid chemical 124 comes in contact with the cell culture medium 104 via permeable portion 109.

Thereafter, the liquid chemical 124 which has fallen to the bottom of the transfer chamber 108 and which is now oxygen deficient, is withdrawn and pumped into third vessel 202 via tube 218. The liquid chemical 124 pumped into third vessel 202 at this time may contain a low percentage of cell culture medium 104 therein. As stated earlier, in the preferred embodiment, the liquid chemical 124 is PFC. PFC is a hydrophobic, denser than water substance, and as such, falls to the bottom of the third vessel 202 through any cell culture medium 104 that is present in third vessel 202. Thereafter, the liquid chemical 124, still oxygen deficient, is returned to the second vessel 122 via tube 230.

The cell culture medium 104, if any is present, stays at the upper region of the third vessel 202. The cell culture medium 104 is then returned to the first vessel 102 via tube 224.

The deficient liquid chemical 124 returned to second vessel 122 is then "recharged" by the oxygen introduced to second vessel 122 by oxygen supply tube 130. Thereafter, the oxygen rich liquid chemical 124 is recirculated back to the transfer chamber 108 as described previously.

Fifth pump 240 and tube 226 ensure that a minimum level of liquid chemical 124 remains in the third vessel 202. This is necessary to ensure PFC is not depleted in vessel 202 so that cell culture medium 104 is not pumped via tube 230 into second vessel 122, which would happen if the level of liquid chemical 124 dropped below (or to) the end of tube 230 in vessel 202.

The foregoing description is intended primary for purposes of illustration. The oxygen delivery systems and method heretofore described may be embodied in other forms or carried out in other ways without departing from the spirit or scope of the invention. Modifications and variations still falling within the spirit or the scope of the invention will be readily apparent to those of ordinary skill in the art.

What is claimed is:

1. A method for delivering a selected gas to a cell culture in a culture medium contained within a first vessel, comprising:

(a) submerging a transfer chamber in the culture medium, said transfer chamber having an inlet portion, an outlet portion and a permeable body portion, said permeable body portion being connected between said inlet portion and said outlet portion to form a substantially enclosed flow path therebetween, said permeable body portion allowing the culture medium to enter said flow path;

(b) enriching a liquid chemical with the selected gas;

(c) pumping said enriched liquid chemical into said inlet portion of said transfer chamber such that said liquid chemical enters said flow path;

(d) contacting said enriched liquid chemical in said flow path with the culture medium such that the selected gas is transferred to the culture medium to produce a depleted liquid chemical; and (e) removing said depleted liquid chemical from said transfer chamber through said outlet portion.

2. The method of claim 1, further comprising the steps of:

(f) recharging said depleted liquid chemical with the selected gas to produce said enriched liquid chemical; and (g) recirculating said enriched liquid chemical to said inlet portion of said transfer chamber and repeating steps (d) through (f) to provide a continuous transfer of the selected gas to the culture medium.

3. The method of claim 2, wherein said step (f) of recharging comprises the steps of:

transferring said depleted liquid chemical to a second vessel; and pumping the selected gas through a supply tube into the depleted liquid chemical in said second vessel.

4. The method of claim 2, wherein said step (d) results in a mixing of said liquid chemical and the culture medium such that a portion of the culture medium is removed from said transfer chamber in step (e), and wherein step (f) of recharging comprises the steps of:

transferring said depleted liquid chemical and the removed portion of the culture medium to a second vessel;

allowing said depleted liquid chemical to settle to a lower portion of the second vessel below the removed portion of the culture medium;

removing the removed portion of the culture medium from an upper portion of said second vessel;

returning the removed portion of the culture medium to said first vessel;

removing said depleted liquid chemical from said lower portion of said second vessel;

transferring said depleted liquid chemical to a third vessel; and pumping the selected gas through a supply tube into the depleted liquid chemical in said third vessel.

5. A method for delivering oxygen to a cell culture in a culture medium contained within a first vessel, comprising:

(a) submerging a transfer chamber in the culture medium, said transfer chamber having an inlet portion and an outlet portion disposed in substantially opposed alignment to provide a flow path therebetween, a permeable portion is positioned between said inlet portion and said outlet portion to substantially enclose said flow path, said permeable portion allowing the culture medium to enter said flow path;

(b) providing an oxygen rich liquid chemical to said inlet portion of said transfer chamber;

(c) contacting said oxygen rich liquid chemical with the culture medium within said transfer chamber such that oxygen is transferred from said oxygen rich liquid chemical to the culture medium, thereby producing an oxygen depleted liquid chemical as oxygen is delivered to the culture medium;

(d) removing said oxygen depleted liquid chemical from said transfer chamber through said outlet portion;

(e) recharging said oxygen depleted liquid chemical with oxygen to produce said oxygen rich liquid chemical; and (f) recirculating said oxygen rich liquid chemical to said inlet portion of said transfer chamber and repeating steps (c) through (e) to provide a continuous transfer of oxygen to the culture medium.

6. The method of claim 5, wherein said step (e) of recharging comprises the steps of:

transferring said depleted liquid chemical to a second vessel; and pumping oxygen through a supply tube into the depleted liquid chemical in said second vessel.

7. The method of claim 5, wherein said step (c) results in a mixing of said liquid chemical and the culture medium such that a portion of the culture medium is removed from said transfer chamber in step (d), and wherein step (e) of recharging comprises the steps of:

transferring said depleted liquid chemical and the removed portion of the culture medium to a second vessel;

allowing said depleted liquid chemical to settle to a lower portion of the second vessel below the removed portion of the culture medium;

removing the removed portion of the culture medium from an upper portion of said second vessel;

returning the removed portion of the culture medium to said first vessel;

removing said depleted liquid chemical from said lower portion of said second vessel;

transferring said depleted liquid chemical to a third vessel; and pumping oxygen through a supply tube into the depleted liquid chemical in said third vessel.

* * * * *